United States Patent
Santos et al.

(10) Patent No.: US 9,763,646 B2
(45) Date of Patent: Sep. 19, 2017

(54) METHOD AND SYSTEMS FOR ADJUSTING A PULSE GENERATED FOR ULTRASOUND MULTI-LINE TRANSMIT

(71) Applicant: General Electric Company, Schenectady, NY (US)

(72) Inventors: Pedro Santos, Trondheim (NO); Jan D'hooge, Mechelen (BE)

(73) Assignee: General Electric Company, Schenectady, NY (US)

(*) Notice: Subject to any disclaimer, the term of this patent is extended or adjusted under 35 U.S.C. 154(b) by 89 days.

(21) Appl. No.: 14/303,392

(22) Filed: Jun. 12, 2014

(65) Prior Publication Data

US 2015/0359521 A1  Dec. 17, 2015

(51) Int. Cl.
*A61B 8/00* (2006.01)
*A61B 8/08* (2006.01)
*A61B 8/14* (2006.01)

(52) U.S. Cl.
CPC .............. *A61B 8/54* (2013.01); *A61B 8/5207* (2013.01); *A61B 8/14* (2013.01); *A61B 8/4488* (2013.01)

(58) Field of Classification Search
USPC ........................................................ 600/447
See application file for complete search history.

(56) References Cited

U.S. PATENT DOCUMENTS

| | | | | |
|---|---|---|---|---|
| 4,242,912 A | * | 1/1981 | Burckhardt | A61B 8/14 310/334 |
| 4,422,332 A | * | 12/1983 | Dubuis | G01S 7/5206 73/625 |
| 5,113,866 A | * | 5/1992 | Hassler | G10K 11/346 600/441 |
| 5,115,416 A | * | 5/1992 | Gehlbach | H04B 11/00 367/103 |
| 5,322,068 A | | 6/1994 | Thiele et al. | |
| 5,522,393 A | * | 6/1996 | Phillips | A61B 8/06 600/455 |
| 5,675,554 A | | 10/1997 | Cole et al. | |
| 5,986,972 A | * | 11/1999 | Li | H04B 7/0682 367/13 |

(Continued)

FOREIGN PATENT DOCUMENTS

| | | |
|---|---|---|
| EP | 2237069 A1 | 10/2010 |
| WO | 2005043188 A1 | 5/2005 |
| WO | 2008075302 A2 | 6/2008 |

OTHER PUBLICATIONS

Misaridis, Thanassis et al., "Complex Pulsing Schemes for High Frame Rate Imaging," Ultrasonics Symposium, 2002. Proceedings, Oct. 2002, 4 pages.

(Continued)

*Primary Examiner* — Joel F Brutus
(74) *Attorney, Agent, or Firm* — McCoy Russell LLP

(57) ABSTRACT

Various methods and systems are provided for ultrasound imaging with multi-line transmit. In one example, a method for ultrasound imaging comprises reducing an acoustic intensity at a position away from an array transducer of a combined beam formed from a plurality of transmit beams emitted by the array transducer in a multi-line transmit event by selectively adjusting one or more pulse parameters of one or more individual transmit beams of the combined beam for a given energy level of the one or more individual transmit beams.

18 Claims, 7 Drawing Sheets

(56) References Cited

U.S. PATENT DOCUMENTS

| | | | |
|---|---|---|---|
| 6,055,861 A | 5/2000 | Banta, Jr. et al. | |
| 6,179,780 B1 | 1/2001 | Hossack et al. | |
| 6,432,056 B1* | 8/2002 | Cooley | G01S 7/52046 600/443 |
| 6,585,648 B1* | 7/2003 | Robinson | G01S 7/52046 600/437 |
| 6,709,395 B2 | 3/2004 | Poland | |
| 2004/0068188 A1* | 4/2004 | Robinson | G01S 7/52028 600/447 |
| 2005/0111846 A1* | 5/2005 | Steinbacher | G01S 7/52046 398/140 |
| 2005/0277835 A1* | 12/2005 | Angelsen | A61B 8/14 600/437 |
| 2008/0114239 A1* | 5/2008 | Randall | G01S 7/52073 600/437 |
| 2009/0099456 A1* | 4/2009 | Burcher | A61B 8/00 600/459 |

OTHER PUBLICATIONS

Misaridis, Thanassis et al., "Use of Modulated Excitation Signals in Medical Ultrasound, Part III: High Frame Rate Imaging" IEEE Transactions on Ultrasonics, Ferroelectrics and Frequency Control, vol. 52, No. 2, Feb. 2005, pp. 208-219.

* cited by examiner

METHOD AND SYSTEMS FOR ADJUSTING A PULSE GENERATED FOR ULTRASOUND MULTI-LINE TRANSMIT

FIELD

Embodiments of the subject matter disclosed herein relate to ultrasound imaging techniques, and more particularly, to multi-line transmit techniques.

BACKGROUND

Medical diagnostic ultrasound is an imaging modality that employs ultrasound waves to probe the acoustic properties of the body of a patient and produce a corresponding image. Generation of sound wave pulses and detection of returning echoes is typically accomplished by an ultrasound probe having an array of transducers. Such transducers typically include electromechanical elements capable of converting electrical energy into mechanical energy for transmission of ultrasonic waves into patient tissue and mechanical energy back into electrical energy when the reflected ultrasonic waves reach the transducers.

Multi-line transmit is a type of ultrasound imaging modality that involves each transducer element transmitting multiple ultrasonic waves during a single transmit event. Transmitting multiple ultrasonic waves during a single transmit event increases the imaging frame rate by simultaneously generating multiple lines of ultrasound data.

However, the multiple waves of the multi-line transmit may interfere with one another and result in increased pressure and intensity on the imaged tissue. The acoustic pressure and/or intensity may be quantified by a mechanical index. Mechanical index is an ultrasound safety parameter that estimates the maximum amplitude of the pressure pulse in tissue and indicates the likelihood of bioeffects such as cavitation that may cause tissue damage. Regulatory agencies such as the United States Food and Drug Administration establish ultrasound regulations that set an upper limit on mechanical index for diagnostic applications. Due to the increased number of ultrasonic waves in a multi-line transmit, interference between the waves may increase the acoustic pressure throughout the body and thus the mechanical index may be higher compared to single-line transmit ultrasound imaging. Furthermore, other acoustic parameters subject to government regulations such as spatial-peak time-averaged intensity, spatial-peak pulse-averaged intensity, total output power, and thermal index may be higher compared to single-line transmit ultrasound imaging. The inventors have recognized the above issues with multi-line transmit methods.

BRIEF DESCRIPTION

In one embodiment, a method for ultrasound imaging comprises reducing an intensity at a position away from an array transducer of a combined beam formed from a plurality of transmit beams emitted by the array transducer in a multi-line transmit event by selectively adjusting one or more pulse parameters of one or more individual transmit beams of the combined beam for a given energy level of the one or more individual transmit beams. In this way, the acoustic pressure and intensity of the combined multi-line transmit beam may be reduced, thereby increasing patient safety.

In another embodiment, a system for ultrasound imaging comprises an array transducer including a plurality of array elements, the array transducer adapted to transmit a plurality of transmit beams in a multi-line transmit event; a transmitter coupled to the array transducer and adapted to apply a separate signal pulse to each array element of the plurality of array elements; a receiver coupled to the array transducer and adapted to receive an echo signal produced by each array element and to form a receive signal by summing separate echo signals produced by each array element; a processor coupled to the receiver and including a filter for transforming the receive signal into a set of signals each attributable to one of the plurality of transmit beams, the processor adapted to process the set of signals to account for differences in the separate signal pulse and to produce an output signal comprising a sum of the processed set of signals; and a controller with computer readable instructions for selectively adjusting a time delay applied to each of the separate signal pulses so that no single transducer element simultaneously transmits each of the plurality of transmit beams.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of multi-line transmit for ultrasound imaging. In particular, methods and systems for adjusting pulse parameters for multiple transmit beams during a multi-line transmit in order to reduce the intensity and pressure of a combined beam formed from the multiple transmit beams are disclosed. For example, reducing the intensity of the combined beam may include reducing one or more of an average intensity, total output power, and/or pressure of the combined beam at a position away from an array transducer emitting the multiple transmit beams. Multi-line transmit may be used with an ultrasound imaging system such as the system shown in FIG. 1. The imaging system may include a phased transducer array that converts electrical signal pulses into acoustic transmit beams. The arrival of the electrical signal pulses to the transducer elements may be time delayed according to a time delay profile so that the beam may be steered, as shown in FIG. 2. Multiple transmit beams may be produced by the ultrasound imaging system using the method shown in FIG. 3. The intensity and pressure of a combined beam formed from an overlap of multiple transmit beams may be reduced by changing the waveform shape of each transmit beam, as shown in FIG. 4. The waveform shape of each transmit beam may be systematically adjusted during each multi-line transmit event by following the approach shown in FIG. 5. Additionally or alternatively, the intensity and pressure of a combined beam formed from an overlap of multiple transmit beams may be reduced by changing the delay line configuration, as shown in FIG. 6. The delay line configuration for multi-line transmit may be systematically adjusted during each multi-line transmit event by following the approach shown in FIG. 7.

Figure 1:
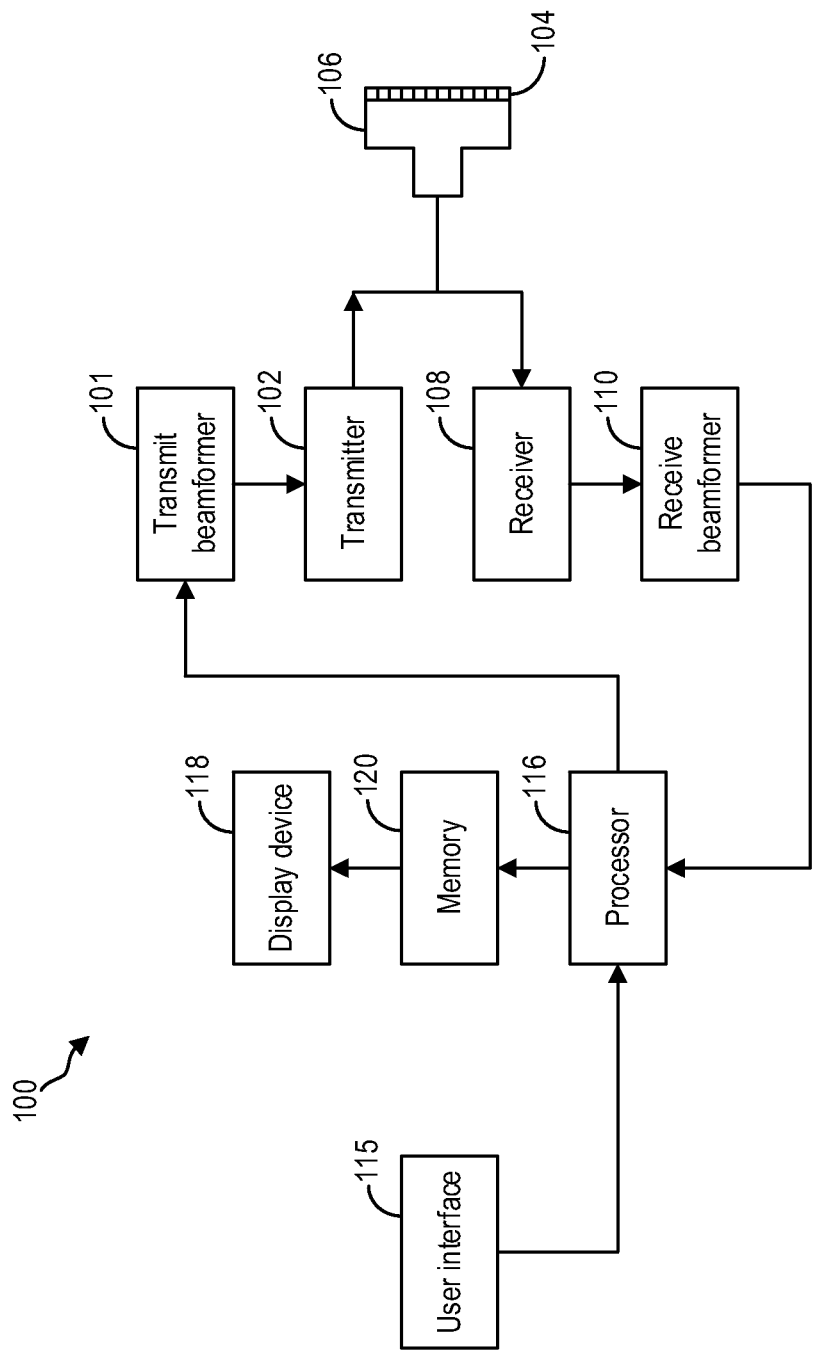
FIG. 1 shows an ultrasonic imaging system according to an embodiment of the invention.
Figure 2:
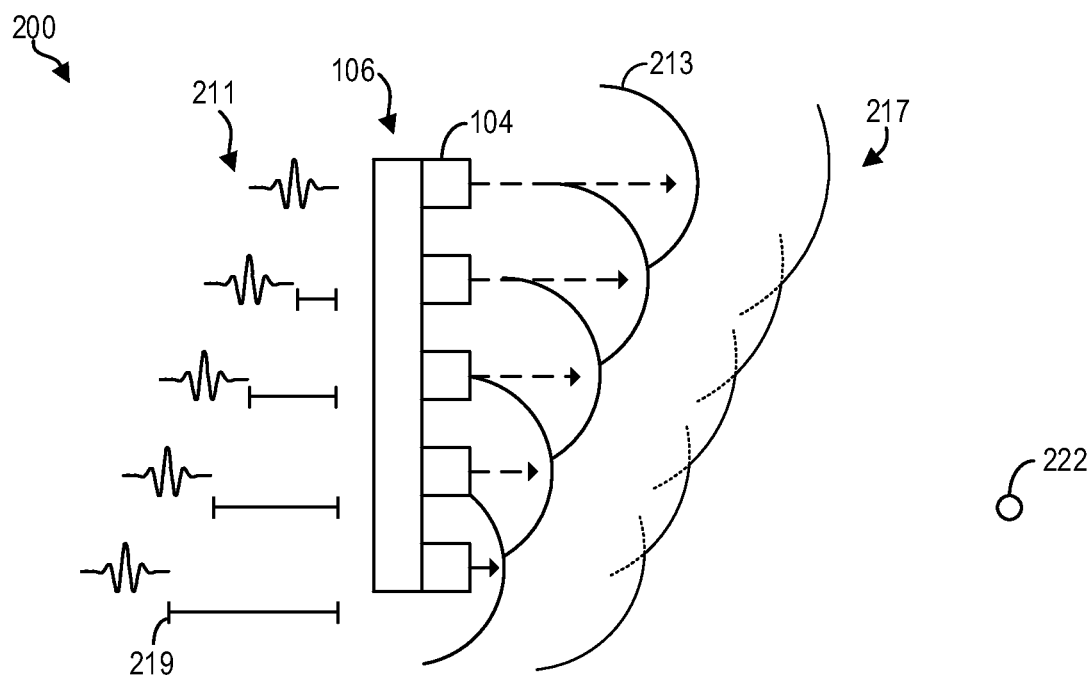
FIG. 2 illustrates a steered beam comprising multiple time-delayed spherical wavefronts according to an embodiment of the invention.
Figure 2:
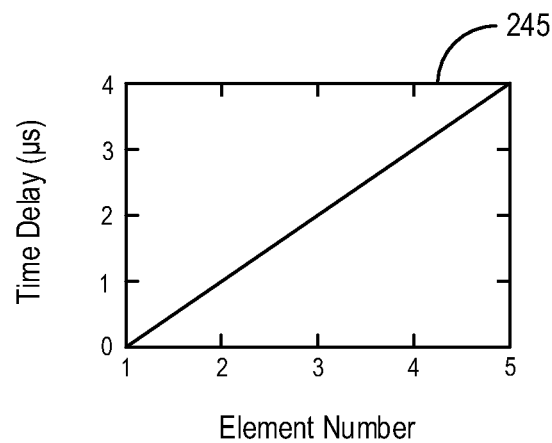

FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown). According to an embodiment, the transducer array 106 may be a one-dimensional transducer array probe. However, in some embodiments, the transducer array 106 may be a two-dimensional matrix transducer array probe. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processor 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

Transducer array 106 may be a phased array. Phased array 106 generates and directs an ultrasonic transmit beam by nearly simultaneously exciting all or most of the elements 104. For the purposes of this disclosure, nearly simultaneous excitation refers to exciting all or most of the elements 104 during a time duration on the order of microseconds. Elements 104 emit ultrasonic spherical wavefronts. If each element 104 is excited at the exact same time, each element 104 emits an identical spherical wavefront propagating in a direction normal to the central element of the phased array. Interference of the spherical wavefronts forms a planar wavefront. The timing sequence of the excitation pulses may be adjusted by adding time delays on the order of microseconds to individual excitation pulses such that the direction of propagation of the planar wavefront can be varied to any desired scan angle. For the purposes of this disclosure, the term "scan angle" is defined as the angle between the direction of propagation and the normal to the central element of the array. Electronic steering and focusing via time delays of transmit beams is discussed further herein and with regard to FIG. 2.

Transducer elements 104 may be capable of emitting multiple ultrasonic beams at once, so that the ultrasound imaging system 100 may be configured with a multi-line transmit mode in addition to or in place of a single-line transmit mode. During a single-line transmit, all elements 104 are excited using identical transmit signals to produce ultrasonic pulses which form a single transmit beam. In contrast, during a multi-line transmit, all elements 104 may be excited using multiple replicas of the identical transmit signals to produce a plurality of ultrasonic pulses to form multiple transmit beams during a single transmit event. In this way, the frame rate of ultrasound imaging may be increased.

FIG. 2 illustrates the formation of a single steered transmit beam using a phased array transducer 106. FIG. 2 includes a schematic 200 illustrating the formation of a single transmit beam using a transducer array 106. As described above with reference to FIG. 1, transducer array 106 includes a number of transducer elements 104, for example, 64 elements or 128 elements. Transducer elements 104 may comprise a piezoelectric crystal. When a voltage is applied to a piezoelectric crystal, the crystal physically expands and contracts, emitting an ultrasonic spherical wave 213. In this way, transducer elements 104 may convert electronic transmit signals into acoustic transmit beams. Transducer elements 104 may also be excited using a current pulse or a pulse-width modulated signal to emit an ultrasonic spherical wave 213.

Exciting each transducer element 104 with an identical transmit signal pulse 211 produces a planar wavefront 217 comprising the sum of all individual spherical wavefronts produced by transducer elements 104. A single transmit beam comprises planar wavefront 217. Transmit beam 217 is directed, or steered, towards target 222 by adjusting the timing delays of transmit signals 211. The time delay 219 of a transmit signal is the time difference between an excitation of an array element by the transmit signal and the excitation of the first element array in a transmit event. For example, the first transmit signal 211 to excite a transducer element 104 has zero time delay, and the last transmit signal 211 to excite a transducer element 104 may have, for example, a five microsecond time delay. Time delays are brief in comparison to the travel time of transmit beam 217, for example the time delays may range from nanoseconds to a few microseconds while the travel time of transmit beam 217 may be 65 microseconds (assuming a constant soft-tissue propagation speed of 1,540 meters per second and a round-trip distance of ten centimeters). The travel time of transmit beam 217 depends on the distance traveled by transmit beam to and from a structure within the body, so in some examples the travel time of transmit beam 217 may be more or less than 65 microseconds. By applying time delays, each individual wavefront may arrive at the target at the same time. For the purposes of this disclosure, time delays are given with respect to the first emitted pulse. An equivalent discussion of time delays may define time delays with respect to the central transducer element, such that time delays may be advanced or retarded with respect to the central element excitation.

During a single-line transmit event, transmit beamformer 101 forms a transmit signal 211 using given parameters such as frequency, phase shift, pulse duration, and the like. Transmitter 102 sends the transmit signal 211 to each transducer element 104 with a time delay 219, as shown in schematic 200. For example, as shown by schematic 200, each transmit signal 211 for each transducer element 104 may have a different length time delay 219. As shown by schematic 200, the top most transducer element 104 has zero delay while the bottom most transducer element 104 has the longest time delay 219. As each transmit signal 211 reaches transducer 106, the corresponding transducer element 104 converts the electrical signal to an acoustic signal, forming a spherical wave 213. Each identical spherical wave 213 interfere to produce a planar wavefront 217 with a constant scan angle.

During a multi-line transmit event, transmit beamformer 101 forms a plurality of transmit signals using given parameters such as frequency, phase shift, pulse duration, and the like. Transmit beamformer 101 may adjust a pulse parameter of one or more of the transmit signals with respect to an unadjusted transmit signal in order to reduce the intensity of interference between the emitted transmit beams. For example, one or more of the transmit signals may be phase shifted or have a different frequency such that constructive interference in the near field is minimized. For the purpose of this disclosure, the term "near field" refers to the region between the transducer and the focal zone where the transmit beams are tightly collimated. Transmitter 102 sends the plurality of transmit signals to each transducer element 104 with each transmit signal appropriately time delayed according to a pre-determined time delay configuration. The pre-determined time delay configuration is such that each transmit beam emitted by transducer elements 104 has a different scan angle but a same focal length. Time delay configurations are discussed further herein with regard to FIGS. 6 and 7.

FIG. 2 further includes a graph 245 illustrating an example delay line configuration corresponding to the steered transmit beam depicted by schematic 200. The delay line defines the firing sequence of the individual elements 104 of a transducer array 106. The delay line, as referred to herein, is defined as the plot of time delay versus element number for a transmit beam emitted by a transducer array. Thus, the delay line shows the time delay for each transducer element of the transducer array. Said another way, the delay line determines an excitation sequence of the plurality of elements of the transducer array, in a specific element order, to form a directed transmit beam. The slope of the delay line defines the scan angle of the corresponding transmit beam. For example, a delay line with zero slope corresponds to a transmit beam with a scan angle of zero such that the transmit beam wavefront is parallel to the transducer, while a delay line with a positive slope corresponds to a transmit beam with a positive scan angle. The curvature of the delay line defines the focal depth of the transmit beam. For example, a delay line with no curvature does not focus at any point, while a delay line with curvature may correspond to a transmit beam that focuses at a focal depth related to the delay line curvature. A delay line may also correspond to a curvature such that the beams diverge from the transducer. The delay line may also be referred to as a delay profile of the transducer array. For example, the delay line of each transmit beam is an excitation delay profile of all the elements of the array. A delay line may be a two-dimensional function in the case of a two-dimensional array transducer. The two-dimensional function may be a convex function defined with respect to a focal depth.

Returning to graph 245, the horizontal axis shows the transducer element and the vertical axis shows the time delay in microseconds. In this example, the entire transmit event lasts for four microseconds. At zero microseconds, a first transducer element is excited. At one microsecond, a second transducer element is excited. At two microseconds, a third transducer element is excited. At three microseconds, a fourth transducer element is excited. At four microseconds, a fifth transducer element is excited. Thus, the firing of the second transducer element is delayed relative to the firing of the first transducer element by one microsecond, the firing of the third transducer element is delayed relative to the firing of the first transducer element by two microseconds, and so on. Regarding schematic 200, the first transducer element is the top transducer element and the fifth transducer element is the bottom transducer element.

During a multi-line transmit event, each transducer element 104 receives a number of transmit signals within a duration of the event. The duration of the multi-line transmit event is determined by the longest time delay, typically no more than a few microseconds. Multi-line transmit increases the frame rate of ultrasonic imaging by increasing the number of scan lines produced during a transmit event. For example, if four transmit beams are produced during multi-line transmit, data for four scan lines may be collected in the same amount of time needed for a single-line transmit to collect data for one scan line. Configurations of delay lines during multi-line transmit are discussed further herein and with regard to FIGS. 6 and 7.

The use of multi-line transmit for diagnostic applications may introduce safety concerns for the tissue of the patient being imaged. In particular, multi-line transmit may have a large mechanical index. Mechanical index is an ultrasound safety parameter proportional to the maximum negative amplitude of the pressure pulse (peak rarefactional pressure) in tissue and indicates the likelihood of mechanical bioeffects such as cavitation that may cause tissue damage. Other acoustic output parameters such as spatial-peak time-averaged intensity and thermal index indicate the likelihood of thermal bioeffects such as tissue heating. Ultrasound regulations established by regulatory agencies such as the United States Food and Drug Administration set an upper limit on all acoustic output parameters related to the safety of diagnostic applications. Due to the increased number of transmit beams in a multi-line transmit, interference between the transmit beams may increase the acoustic pressure throughout the body and thus acoustic output may be higher compared to single-line transmit particularly close to the transducer where the different transmit beams overlap. However, peak negative pressure, as well as spatial-peak pulse-average intensity and spatial-peak time-average intensity, throughout the tissue can be reduced by reducing an intensity of a combined beam formed from a plurality of transmit beams in a multi-line transmit event. In one example, the intensity of the combined beam for the multi-line transmit event may be reduced by selectively adjusting one or more pulse parameters of one or more individual transmit beams of the combined beam (for a given energy level of the one or more individual transmit beams) so that at least one of the individual transmit beams is different than the other individual transmit beams. Methods for reducing interference between transmit beams during a multi-line transmit, and thus reducing the intensity, are disclosed herein.

Figure 3:
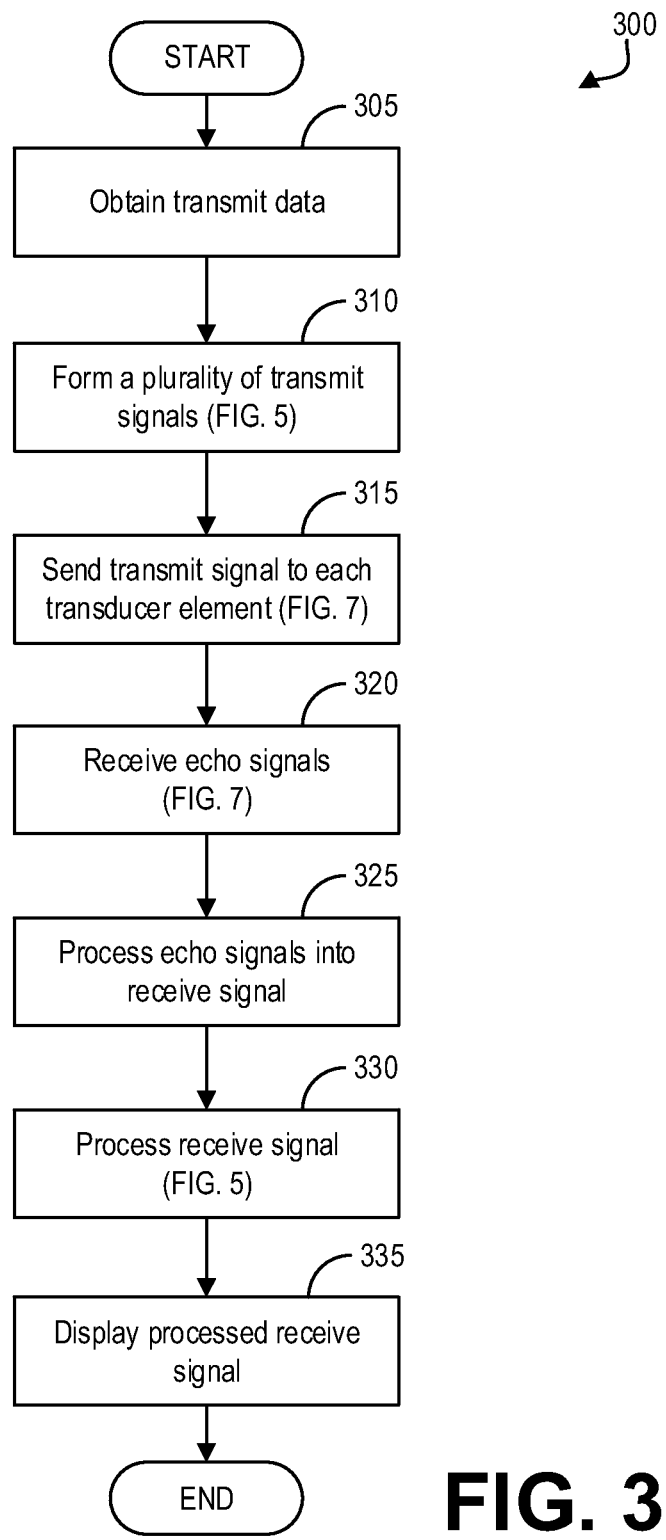
FIG. 3 shows a high-level flow chart for performing multi-line transmit according to an embodiment of the invention.
Figure 4:
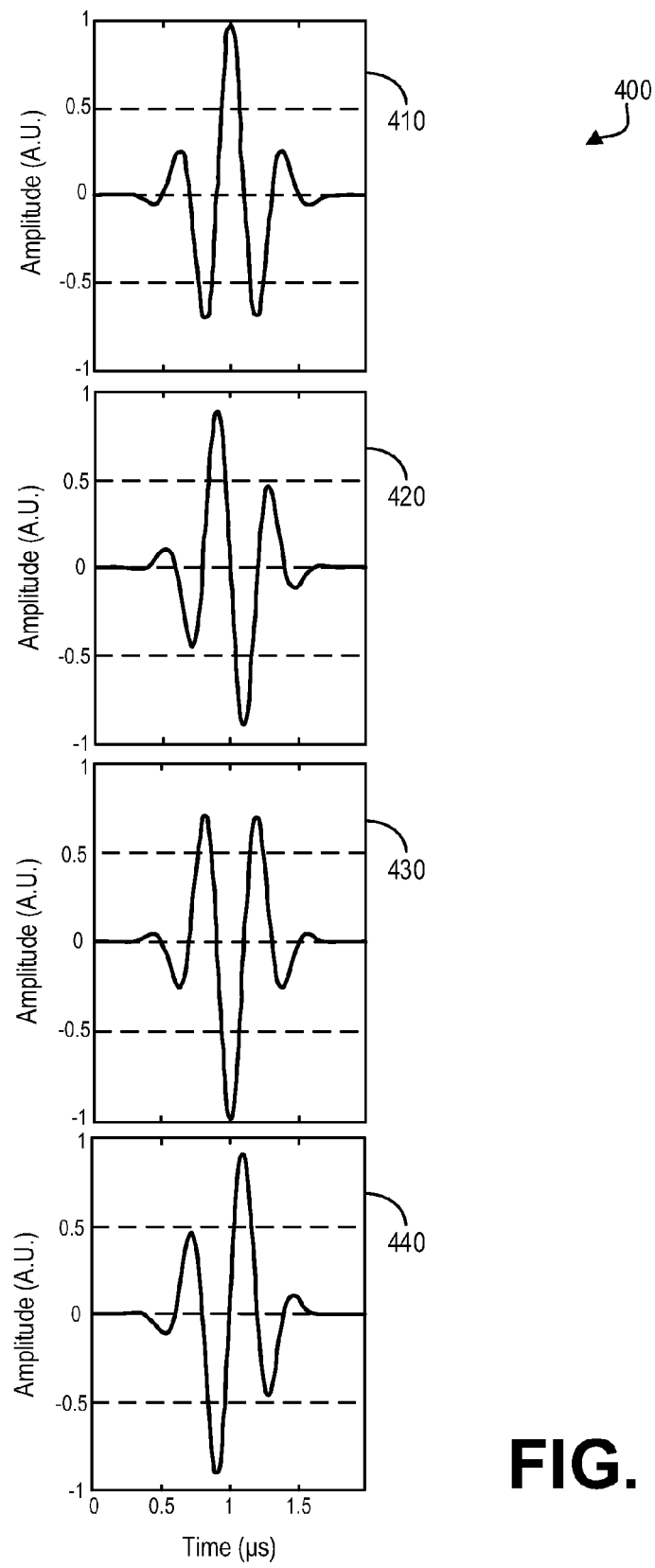
FIG. 4 shows a set of graphs illustrating a plurality of transmit beams with different phase shifts according to an embodiment of the invention.

FIG. 3 is a flow chart of an embodiment of a multi-line transmit ultrasound method 300. Method 300 will be described herein with reference to the system depicted in FIG. 1, though it should be understood that the method may be applied to other systems without departing from the scope of this disclosure. Method 300 may be carried out by processor 116, and may be stored as executable instructions in non-transitory memory of the processor 116.

Method 300 begins at 305. At 305, the method 300 may include obtaining transmit data. Transmit data may include, but is not limited to, a desired frame rate (i.e., a desired number of transmit beams), the shape of the transmit beams, delay line configurations (i.e., desired scan angles), and focal depth. Obtaining transmit data may include receiving input parameters regarding the ultrasound imaging session via user interface 115, obtaining transmit data stored in non-transitory memory, or a combinations thereof. After obtaining the transmit data, method 300 may continue to 310.

At 310, method 300 may include forming a plurality of transmit signals using transmit beamformer 101. The number of transmit signals formed depends on the desired number of transmit beams. For example, to obtain data for four scan lines, four transmit beams must be used. To create four transmit beams, transmit beamformer must form four transmit signals. In conventional multi-line transmit, the four transmit signals are identical replicas. However, forming a plurality of transmit signals may include adjusting a pulse parameter for one or more of the transmit signals. As such, one transmit signal may have a different pulse parameter than another of the transmit signals for the same transmit event. In one example, the waveform shape may be adjusted for one or more of the transmit signals, relative to the waveform shape of other of the transmit signals, in order to reduce the intensity of interference within the body below a safety threshold. Adjusting the waveform shape may include changing the phase shift of a transmit signal, changing the frequency of a transmit signal, combinations thereof, and the like. Adjusting the waveform shape of a plurality of transmit signals is discussed further herein with regard to FIGS. 4 and 5. Further, transmit apodization may be applied. Apodization, or windowing, comprises defining a different weight for each transducer element so that not all elements are actuated with the same voltage amplitude. For example, the excitation voltage to the central transducer elements may be maximized and reduced toward the peripheral transducer elements. Method 300 may then continue to 315.

At 315, method 300 may include sending the plurality of transmit signals to each transducer element. After forming the plurality of transmit signals using transmit beamformer 101, transmitter 102 sends the plurality of transmit signals to each transducer element 104. For example, if four transmit signals are formed with transmit beamformer 101, transmitter 102 sends the four transmit signals to each transducer element 104. Each transducer element 104 produces a plurality of ultrasonic pulses to form a plurality of transmit beams. For example, if there are four transmit signals, each transducer element 104 produces four ultrasonic pulses. The four pulses produced by each transducer element 104 interfere to create four transmit beams that may have different scanning angles. Transmitter 102 applies time delays, according to a delay line configuration (e.g., excitation delay profile of the transducer array), to each transmit signal sent to each transducer element 104 such that each transmit beam may have a different scanning angle determined by the delay line for each transmit beam. In conventional multi-line transmit, each delay line is determined using a single focal depth. As a result, the central transducer element may simultaneously transmit all of the plurality of transmit pulses. However, in one example, the configuration of delay lines may be adjusted to have the same focal depth while allowing each transducer element to simultaneously emit at most two of the plurality of transmit pulses. In this way, the acoustic intensity may be reduced in the near field. Adjusting the delay line configurations is discussed further herein and with regard to FIGS. 6 and 7. Method 300 may then continue to 320.

At 320, method 300 may include receiving echo signals. The transmit beams travel through tissue and are back-scattered off structures within the body to form echoes. Transducer elements 104 convert the acoustic echoes into electrical echo signals which are sent to receiver 108. Receiver 108 retrospectively focuses the echo beams by aligning the echo signals. Receiver 108 aligns the echo signals by applying time delays to each echo signal according to the time delay applied to the corresponding transmit signal. If the time delay configurations were adjusted at 315, method 300 may include applying the corresponding adjusted time delays to the echo signals. Applying the corresponding adjusted time delays to the echo signals is discussed further herein and with regard to FIG. 7. Method 300 may then continue to 325.

At 325, method 300 may including processing the echo signals into a receive signal. Receive beamformer 110 may sum the echo signals, adjusted for time delays, to produce a large-amplitude radio-frequency (RF) receive signal for each of the plurality of transmit signals. For example, if four different transmit signals were initially transmitted, receive beamformer 110 forms four different receive signals. However, multi-line acquisition may be used, that is, the number of receive signals formed by receive beamformer 110 may be greater than the number of transmit beams transmitted by transmitter 102. Further, receive apodization may be applied to the echo signals. Method 300 may then continue to 330.

At 330, method 300 may include processing the receive signals. Processing the receive signal requires knowledge of how the transmit signals were formed and is discussed further herein with regard to FIGS. 5 and 7. For example, processing the receive signals may include matching the frequencies and/or phase shifts of the plurality of receive signals. Processing the receive signals may further include converting the ultrasound data into an image for display using signal processing techniques such as time-gain compensation, compression, gray-scale mapping, and spatial compounding.

After processing the receive signals, the method 300 may continue to 335, where the method may include displaying the image formed from the processed receive signals on display device 118 (shown in FIG. 1). It should be appreciated that the display 118 may only show a portion of the processed image and that the processor 116 may use a range of display techniques and modes, such as B-mode, Color Doppler, power Doppler, M-mode, spectral Doppler, anatomical M-mode, 3D-mode, 4D-mode, strain, and strain rate when displaying the processed image. Method 300 may then end.

FIG. 4 shows a set of graphs 400 illustrating an example plurality of transmit signals with different waveform shapes in accordance with the current disclosure. In particular, four transmit signals with different phase shifts are shown.

In this example, three of the four total transmit signals are phase shifted with respect to an unadjusted transmit signal. Graph 410 shows a first transmit signal comprising a Gaussian pulse with a two microsecond duration. Graph 420 shows a second transmit signal including the first transmit signal of graph 410 with a sinusoidal term including a $\pi/2$ phase shift. Graph 430 shows a third transmit signal including the transmit signal of graph 410 with a sinusoidal term including a it phase shift. Graph 440 shows a fourth transmit signal including the transmit signal of graph 410 with a sinusoidal term including a $3\pi/2$ phase shift. As a result of applying the different phase shifts, a peak amplitude of each different transmit signal is shifted relative to the other transmit signals. In particular, the transmit signal shown in graph 410 is the inverse of the transmit signal shown in graph 430, and the transmit signal shown in graph 420 is the inverse of the transmit signal shown in graph 440. In this way, the waveform shape of each transmit signal is adjusted such that the sum of the four transmit signals has a reduced amplitude. In this example, the sum of the four transmit signals has zero amplitude. In other embodiments, the sum of the transmit signals may have an amplitude greater than zero.

In this embodiment, the multi-line transmit includes four transmit signals with different phase shifts. Other embodiments may include more or less than four transmit signals for multi-line transmit. In some embodiments, two or more of the transmit signals may have the same phase shift. For example, while the set of phase shifts $\{0, \pi/2, \pi, 3\pi/2\}$ is shown in FIG. 4, other embodiments may use sets of phase shifts such as $\{3\pi/2, \pi, \pi/2, 0\}$, $\{0, \pi, 0, \pi\}$, $\{\pi/2, 3\pi/2, \pi/2, 3\pi/2\}$, $\{0, \pi, \pi/2, 3\pi/2\}$, $\{0, \pi, \pi, 0\}$, $\{0, \pi/4, \pi/2, 3\pi/4\}$, $\{0, 2\pi/3, 4\pi/3, 0\}$, $\{\pi/2, \pi, 0, \pi/2\}$, $\{\pi/2, \pi, 0, 3\pi/2\}$, $\{\pi, 0, 0, \pi\}$, and so on. The choice of which phase shift set to use may depend on the acoustic intensity produced by the transmit beams, and therefore may depend on other pulse parameters such as focal depth, time delay line configuration, and scan angles.

The waveforms shown in FIG. 4 were formed using a Gaussian profile, however another type of waveform pulse profile may be used. In general, all waveform pulse profiles include an oscillatory component wherein a phase shift may be applied.

Figure 5:
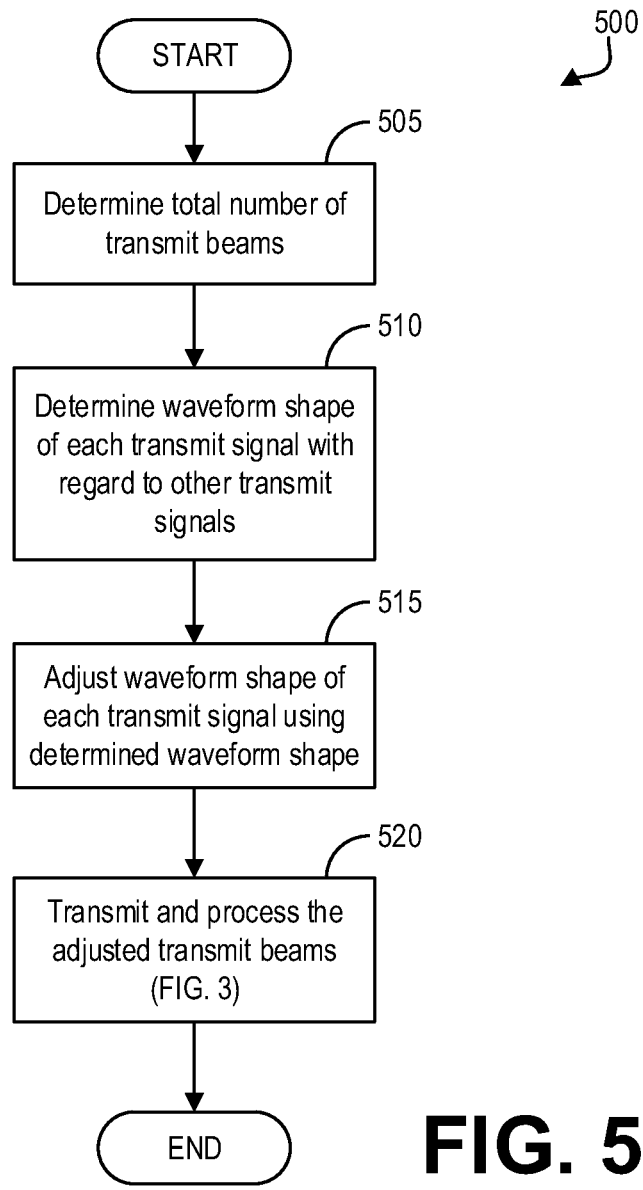
FIG. 5 shows a high-level flow chart for preparing a multi-line transmit beam comprising a plurality of transmit beams with adjusted waveform shapes according to an embodiment of the invention.
Figure 6:
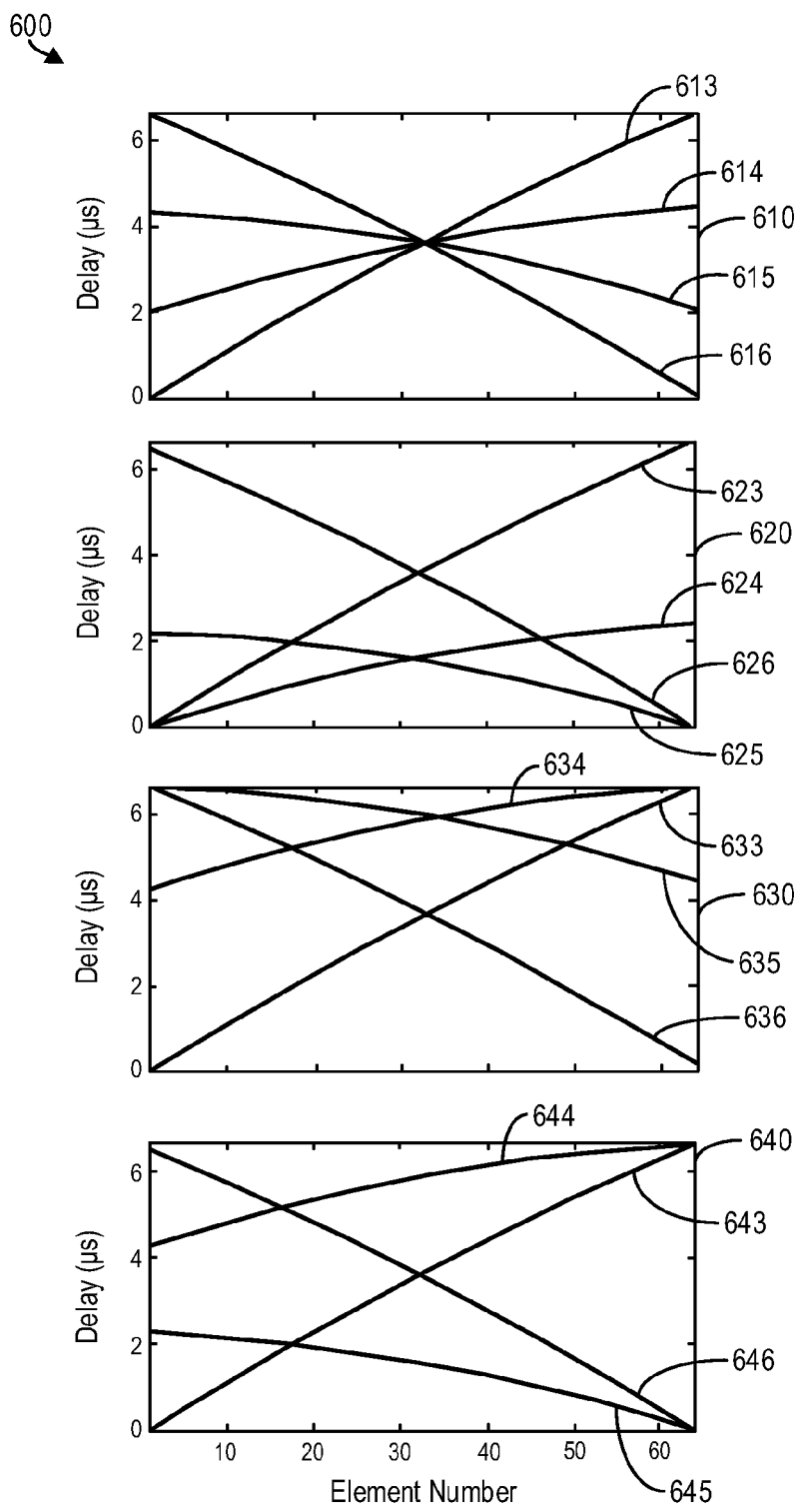
FIG. 6 shows a set of graphs illustrating example time delay configurations according to an embodiment of the invention.

FIG. 5 is a flow chart of an embodiment of an ultrasound multi-line transmit method 500 for adjusting the waveform shape of a plurality of transmit beams. Method 500 will be described herein and with reference to the system depicted in FIG. 1 and the method depicted in FIG. 3, though it should be understood that the method may be applied to other systems and methods without departing from the scope of this disclosure. Method 500 may be carried out by processor 116, and may be stored as executable instructions in non-transitory memory of the processor 116.

Method 500 may begin at 505 by determining the total number of transmit beams. The total number of transmit beams may correspond to the number of directions that are to be acquired in one transmit event. The total number of transmit beams in a single multi-line transmit event may include at least two transmit beams. Method 500 may then continue to 510.

At 510, method 500 may include determining the waveform shape of each transmit signal with regard to the waveform shape of other transmit signals. For example, the method at 510 may include determining a waveform shape adjustment to apply to each transmit signal corresponding to each transmit beam of a single multi-line transmit event. The waveform shape of one or more transmit beams may be changed by changing the waveform shape of the corresponding transmit signal, and may be changed such that the shape of the one or more individual transmit beams has a maximal amplitude offset from a maximal amplitude of an unadjusted (or differently adjusted) individual transmit beam. Changes in waveform shape may comprise a phase or frequency shift of a transmit signal. The waveform shape of each transmit signal may be determined with regard to other pulse parameters of the transmit signals such as delay line configuration. For example, if a delay line configuration includes the central transducer element simultaneously emitting each transmit beam, the set of phase shifts shown in FIG. 4 may be chosen such that the acoustic intensity in the region adjacent to the central element is reduced. In other examples, the delay lines may be configured such that a transducer element may simultaneously emit at most two transmit beams. In such examples, the set of phase shifts may be determined such that the acoustic intensity in the region adjacent to an element simultaneously emitting two transmit beams is reduced.

In one embodiment, determining the waveform shape of each transmit signal may include determining a phase shift of each transmit signal. For example, as described above with reference to FIG. 4, a phase shift of each transmit signal (and resulting transmit beam) may be selected such that a phase shift of one transmit beam is different than at least one other transmit beam. In other examples, the phase shift of each transmit beam is different than all other transmit beams, more than one transmit beam has the same phase shift different from at least one other transmit beam, and the like. As discussed above with regard to FIG. 4, example phase shifts for a four-line multi-line transmit may be $\{0, \pi/2, \pi, 3\pi/2\}$, $\{3\pi/2, \pi, \pi/2, 0\}$, $\{0, \pi, 0, \pi\}$, $\{\pi/2, 3\pi/2, \pi/2, 3\pi/2\}$, $\{0, \pi, \pi/2, 3\pi/2\}$, $\{0, \pi, \pi, 0\}$, $\{0, \pi/4, \pi/2, 3\pi/4\}$, $\{0, 2\pi/3, 4\pi/3, 0\}$, $\{\pi/2, \pi, 0, \pi/2\}$, $\{\pi/2, \pi, 0, 3\pi/2\}$, $\{\pi, 0, 0, \pi\}$, and so on.

In another embodiment, determining the waveform shape of each transmit signal may include determining a frequency shift of each transmit signal. The attenuation of the transmit beam within the body is frequency dependent, and different frequencies may have different attenuation coefficients. In order to maintain a same intensity in the focal region for all transmit beams, the frequency shifts may be determined such that the attenuation coefficients are within a threshold range, for example 1% or 2%. Shifting the frequency may change the waveform shape of a transmit beam, though maintaining the attenuation coefficient of each transmit beam within a threshold range restricts the magnitude of possible frequency shifts. In another example, the frequency shift may be significant and so, compensation for the different attenuation coefficients may be required.

The waveform shapes of the transmit beams are determined in order to change the interference pattern of the transmit beams within the body. In particular, the interference pattern of the transmit beams is changed such that one or more acoustic output parameters, such as intensity, of the combined beam formed from the plurality of transmit beams is reduced for a given energy level of the one or more individual transmit beams. More specifically, the method at 510 may include selecting a specific shape (e.g., phase shift, frequency, or the like) of each transmit beam of the plurality of transmit beams in a single multi-line transmit event to reduce one or more acoustic output parameters, such as intensity, of the combined beam at a position away from the transducer away (e.g., at position in a target tissue). The intensity may be the peak negative pressure, spatial-peak pulse-average intensity, spatial-peak time average intensity, and the like. Waveform shapes of each transmit beam are determined such that all acoustic output parameters of the combined beam comprising each of the transmit beams are reduced below safety thresholds. In this way, selecting the waveform shape of each transmit beam in a single multi-line transmit event may be based on one or more safety intensity thresholds.

After determining the waveform shape of each transmit signal, method 500 may then continue to 515, where method 500 may include adjusting the waveform shape of each transmit signal using the determined waveform shape adjustment. In some examples, the waveform shape of one or more transmit signals is adjusted. For example, the waveform shape of at least one transmit signal may be different than the waveform shape of the other transmit signals in a single multi-line transmit event. In other examples, the waveform shape of each transmit signal is adjusted. For example, the waveform shape of each individual transmit signal may be different than the waveform shape of every other transmit signal in the same multi-line transmit event. Thus, the resulting transmit beams may have shapes that overlap less than multi-line transmits using identical transmit beams.

Transmit beamformer 101 performs waveform shape adjustments when forming transmit signals. Method 500 may then continue to 520.

At 520, method 500 may include transmitting and processing the adjusted transmit beams. Transmitting and processing the adjusted transmit beams may be performed according to the method shown in FIG. 3. For example, transmitter 102 sends the plurality of transmit signals with adjusted waveform shapes to transducer 106 after applying steering and focusing time delays. Each transducer element 104 converts each electrical transmit signal into an acoustic waveform. The plurality of acoustic waveforms formed from a single transmit signal interfere to produce a single transmit beam. Using four-line multi-line transmit with 64 transducer elements as an example, each element converts four individual transmit signals into four acoustic waveforms; the 64 waveforms associated with an individual transmit signal form an individual transmit beam sharing the waveform characteristics of the transmit signal. The individual transmit beams form a combined beam with a reduced acoustic output (i.e., mechanical index, averaged intensity and the like) throughout the tissue due to the waveform adjustments determined at 510 and applied at 515. The transmit beams reflect off structures in the body and return to the transducer elements 104, which convert the acoustic echoes into electrical signals. The electrical signals may be time delayed by the receiver 108 to temporally align the echo signals. Receive beamformer 110 may sum the echo signals to produce a receive signal. There may be one or more receive signal corresponding to each transmit signal. Processor 116 may process the receive signals in order to account for the different waveform shapes of the transmit beams when generating the resulting ultrasound image. In one example, if one of the transmit signals was phase shifted, processor 116 may apply a phase shift to the receive signal such that all receive signals have the same phase before further processing the receive signals. In another example, if one of the transmit signals was phase shifted, processor 116 may process the receive signals without phase shifting the corresponding receive signal, thus being the corresponding receive lines formed with such phase. A processing of the received signals regarding the phase shifts may depend on the ultrasound mode (B-mode, color Doppler, M-mode, strain, strain rate and the like). Processing the receive signals may further include converting the ultrasound data into at least one image for display using signal processing techniques such as time-gain compensation, compression, gray-scale mapping, and spatial compounding. The image or images may then be displayed on a display device 118. Method 500 may then end.

FIG. 6 is a set of graphs of different time delay line configurations 600 for ultrasound multi-line transmit events in accordance with the current disclosure. As shown in FIG. 6, each delay line configuration illustrates the excitation sequence for 64 transducer elements to produce four transmit beams. Each transducer element emits four pulses during a single multi-line transmit event including four transmit beams. Additionally, each delay line corresponds to a transmit beam with a different scan angle. Further, each transmit beam shown in FIG. 6 has the same focal depth and thus the same curvature. In another example, focal depths may be different for one or more transmit beams and thus the curvatures may be different.

Changing the delay line configuration of the transmit beams in a multi-line transmit event can reduce the number of overlapping transmit beams and therefore reduce the acoustic intensity especially in the near field, thereby decreasing potential tissue damage. In some embodiments, each transmit beam is identical except for the delay line configuration and thus the scan angle. In other embodiments, one or more of the transmit beams may have one or more pulse parameters, such as the phase, adjusted to further reduce acoustic intensity in the near field.

Graph 610 is an example of a conventional delay line configuration. Line 613 shows a first transmit beam, line 614 shows a second transmit beam, line 615 shows a third transmit beam, and line 616 shows a fourth transmit beam. Each delay line of each transmit beam intersects at the central element (in this example, element 31/32). That is, the central element simultaneously emits more than one transmit beam. Depending on the pulse duration, more than one pulse may partially be transmitted simultaneously for the elements adjacent to the central one. In the example shown, the central element simultaneously emits all four transmit beams. If the plurality of transmit beams is identical, the transmit beams will sum to produce a large-amplitude combined beam in the region adjacent to the central element, thereby increasing the intensity in the tissue. However, if the waveform shapes of the plurality of beams are adjusted as discussed herein with regard to FIG. 5, the transmit beams will sum to produce a lower-amplitude combined beam in the region adjacent to the central element, thereby decreasing the intensity in the tissue.

Graph 620 is an example of a delay line configuration with all of the beams aligned in the front. For the purpose of this disclosure, the phrase "in the front" refers to the intersection of delay lines closer to or at the beginning of the multi-line transmit event. Note that the first transmit beam 623 is the same as the first transmit beam 613 shown in graph 610, and that the duration of the multi-line transmit event is similarly unchanged. The delay lines in graph 620 are configured to cross pair-wise, that is, each intersection includes only two transmit beams. First transmit beam 623 and second transmit beam 624 intersect at element 1 with zero delay, while third transmit beam 625 and fourth transmit beam 626 intersect at element 64 with zero delay. That is, at the beginning of the multi-line transmit event (zero delay), element 1 simultaneously emits the first and second transmit beams 623 and 624 while element 64 simultaneously emits the third and fourth transmit beams 625 and 626. First transmit beam 623 intersects third transmit beam 625 after two microseconds and intersects fourth transmit beam 626 after four microseconds. Fourth transmit beam 626 also intersects second transmit beam 624 after two microseconds. Second transmit beam 624 and third transmit beam 625 intersect after two microseconds. That is, the central element simultaneously emits the second and third transmit beams 624 and 625 two microseconds after the start of the multi-line transmit event and the first and fourth transmit beams 623 and 626 four microseconds after the start of the multi-line transmit event. Element 18 simultaneously emits the first and third transmit beams 623 and 625 after two microseconds, and element 58 simultaneously emits the second and fourth transmit beams 624 and 626 after two microseconds. By configuring the delay lines to cross pair-wise rather than all at once, the intensity of the combined beam formed from the plurality of transmit beams is reduced. For example, even if the transmit beams are identical in waveform shape, the amplitude of the overlapping transmit pulse produced at the array element at each intersection may be half the amplitude produced at the intersection in graph 610. The amplitude, and therefore the pressure, intensity, and one or more acoustic output parameters, may be further reduced by adjusting the waveform shape as discussed herein with regard to FIG. 5. For example, fourth transmit beam 626 intersects first transmit beam 623, second transmit beam 624, and third transmit beam 625. If the waveform shape of fourth transmit beam 626 is adjusted with respect to the three other transmit beams such that the maximal amplitude of fourth transmit beam 626 is offset from the maximal amplitude of the three other transmit beams, then the combined amplitude produced by the overlap of fourth transmit beam 626 with the other transmit beams at the three intersections may be significantly reduced. In this way, the intensity of a combined beam formed from a plurality of transmit beams in a multi-line transmit event may be reduced by selectively adjusting the delay lines of one or more individual transmit beams of the combined beam for a given energy level of the one or more individual transmit beams while maintaining the transmit event duration. The focal depth of each of the individual transmit beams may also be maintained.

Graph 630 is an example of a delay line configuration with all of the beams aligned in the back. For the purpose of this disclosure, the phrase "in the back" refers to the intersection of close to or at the end of the multi-line transmit event. The delay lines in graph 630 are configured to cross pair-wise, that is, each intersection includes only two transmit beams. At the end of the multi-line transmit event, first transmit beam 633 and second transmit beam 634 intersect at element 64 while third transmit beam 635 and fourth transmit beam 636 intersect at element 1. That is, at the end of the transmit event, element 1 simultaneously emits the first transmit beam 633 and the second transmit beam 634 while element 64 simultaneously emits the third transmit beam 635 and the fourth transmit beam 636. Similarly, second transmit beam 634 and fourth transmit beam 636 intersect at element 18, first transmit beam 633 and fourth transmit beam 636 intersect at the central element, second transmit beam 634 and third transmit beam 635 intersect at the central element, and first transmit beam 633 and third transmit beam 635 intersect at element 58.

Graph 640 is an example of a delay line configuration with two beams aligned in the front and two beams aligned in the back. The delay lines in graph 640 are configured to cross pair-wise, that is, each intersection includes only two transmit beams. First transmit beam 643 and second transmit beam 644 intersect at the end of the multi-line transmit event at element 64, while third transmit beam 645 and fourth transmit beam 646 intersect at the beginning of the multi-line transmit event at element 64. At element 18, first transmit beam 643 and third transmit beam 645 intersect after two microseconds, and second transmit beam 644 and fourth transmit beam 646 intersect after 5 microseconds. At element 32, first transmit beam 653 intersects fourth transmit beam 646 after 4 microseconds.

The delay line configuration selected for a multi-line transmit event (e.g., the delay line configuration shown in graph 620, 630, or 640) may be based on one or more of the type of ultrasound application (e.g., 3D or 2D ultrasound), the type of the target tissue being imaged, a size of the tissue, a number of multiple transmit beams, an orientation for the transmit beams, or the like. For example, under a first set of conditions, the delay line configuration shown in graph 630 may be selected for a first multi-line transmit event. The first set of conditions may include a significant angular spacing of the plurality of transmit beams. Under a second set of conditions, different than the first set of conditions, the delay line configuration shown in graph 640 may be selected for a second multi-line transmit. The second set of conditions may include a large number of multiple transmit beams. Additionally or alternatively, it may include a non-uniform angular spacing of the transmit beams. In some other set of conditions, the delay lines may be shifted to positions other than "front" or the "back", thus being in intermediate timing. Such a set of conditions may imply a configuration with a large number of multiple transmit beams.

FIG. 6 shows delay line configurations for a transducer array having 64 transducer elements and for a multi-line transmit event including four total transmit beams. However, other delay line configurations for four-line multi-line transmit with a 64-element transducer are possible. Furthermore, it should be noted that FIG. 6 shows one possible embodiment of delay line configurations for a multi-line transmit event and other embodiments are possible. For example, in alternate embodiments, a different transducer array with a different number of transducer elements may have similar delay line configurations as those shown in FIG. 6 and discussed above. Additionally, in alternate embodiments, a single multi-line transmit event may include more or less than four transmit beams. As such, a corresponding number of delay lines to the number of transmit beams may be adjusted relative to one another. In such examples, conventional multi-line transmit has all delay lines intersecting at the central element as shown in 610, while the configurations may be adjusted by forming a plurality of intersections between delay lines as shown in graphs 620, 630, and 640. As long as the number of transmit beams simultaneously emitted by a given intersection is reduced, the interference pattern of the transmit beams may be changed such that the intensity of the combined beam is reduced thus reducing one or more acoustic output parameters (for example mechanical index, pressure, spatial-peak time-averaged intensity, spatial-peak pulse-averaged intensity, total output power, thermal index, and the like). These acoustic output parameters may be determined at a position within the tissue and away from the surface of the array transducer emitting the transmit beams.

The delay line configurations described hereinabove maintain a same focal depth for each transmit beam. However, in one embodiment, the focal depth of one or more of the transmit beams may be adjusted relative to the other beams in order to reduce the intensity of the combined beam formed from the plurality of transmit beams. Adjusting the focal depth of the one or more individual transmit beams comprises changing a curvature of a delay line associated with the one or more individual transmit beams. In one example, the focal depth of each transmit beam may be adjusted with respect to each other. In such an example, the curvature of each delay line may be adjusted with respect to each other. In another example, the focal depth of more than one transmit beam may be adjusted with respect to an unadjusted transmit beam. Such adjustments may give different interference patterns and so may reduce the intensity of the combined beam. Furthermore, such adjustments to the focal depth of one or more transmit beams may allow for a wider variety of delay line configurations than those shown in FIG. 6.

Figure 7:
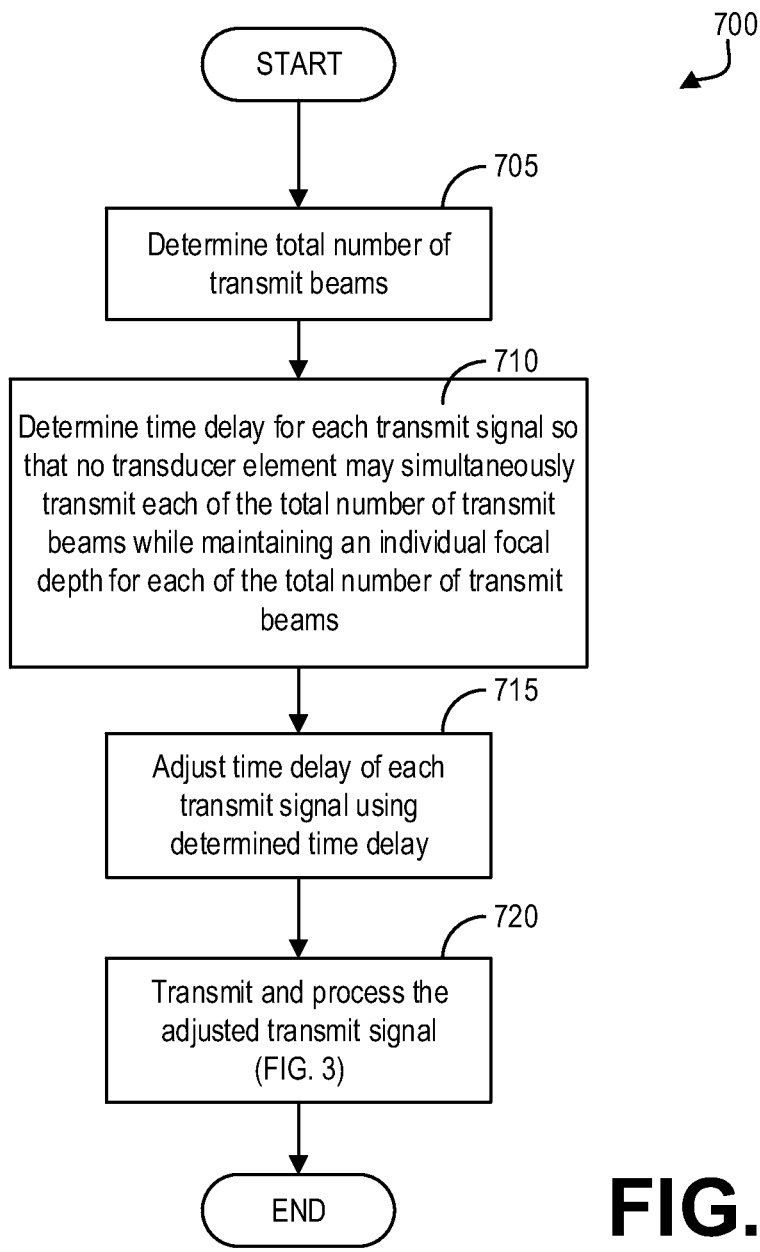
FIG. 7 shows a high-level flow chart for preparing a multi-line transmit beam comprising a plurality of transmit beams with adjusted time delays according to an embodiment of the invention.

FIG. 7 is a flow chart of an embodiment of an ultrasound multi-line transmit method 700 for adjusting the time delay lines for a plurality of transmit beams. Method 700 will be described herein and with reference to the system depicted in FIG. 1 and the method depicted in FIG. 3, though it should be understood that the method may be applied to other systems and methods without departing from the scope of this disclosure. Method 700 may be carried out by processor 116, and may be stored as executable instructions in non-transitory memory of the processor 116.

Method 700 may begin at 705. At 705, method 700 may include determining the total number of transmit beams. The total number of transmit beams corresponds to the number of scan lines acquired during a multi-line transmit event. Method 700 may then continue to 710.

At 710, method 700 may include determining the time delay for each transmit signal such that no transducer element may simultaneously transmit each of the total number of transmit beams while maintaining an individual focal depth for each of the total number of transmit beams. Determining the time delay for each transmit signal may include maintaining the duration of the multi-line transmit event and the curvature of each delay line. Furthermore, determining the time delay for each transmit signal may depend on the total number of transmit beams. For example, the delay lines may be configured to intersect pair-wise, that is, transducer elements 104 may be constrained to simultaneously emit at most two transmit beams. Choice of delay line configuration for a plurality of transmit beams may depend on one or more acoustic output parameters of interference between the transmit beams. For example, time delays may be selected to reduce the mechanical index below threshold levels regulated by the Food and Drug Administration. In another example, time delays may be selected to reduce the mechanical index of the resulting combined beam below a level produced by identical unadjusted transmit beams. In yet another example, time delays may be selected to reduce the spatial-peak time-average intensity of the resulting combined beam below the regulatory threshold levels. Choice of delay line configuration may further depend on the desired scan angles, the focal depth of the transmit beams, the waveform shape of the transmit beams, and combinations thereof. For example, if one of the transmit beams has an adjusted phase shift with respect to the other transmit beams, the delay lines may be adjusted such that the phase shifted transmit beam delay line intersects each other delay line one at a time. In this way, the intensity of the combined beam formed from the plurality of transmit beams may be reduced. Determining the time delay for each transmit signal may further include increasing the total transmit time of the multi-line transmit event. The total transmit time of the multi-line transmit event may be increased to allow different focal depths and delay line configurations. Delay line configurations for four transmit beams are discussed further herein above and with regard to FIG. 6. Method 700 may then continue to 715.

At 715, method 700 may include adjusting the time delay of each transmit signal using the determined time delay. For example, transmit beamformer 101 forms a plurality of transmit signals. Transmitter 102 sends the plurality of transmit signals to transducer 106 after applying the time delays determined at 710. Method 700 may then continue to 720.

At 720, method 700 may include transmitting and processing the adjusted transmit signals. Transmitting and processing the adjusted transmit signals may be performed according to the method shown in FIG. 3. In particular, the time delay configurations determined at 710 may be applied to echo signals received by transducer elements 104 such that each transmit beam is temporally aligned. For example, after the time delays are applied to the transmit signals at 715, each transducer element 104 converts each electrical transmit signal into an acoustic waveform. The plurality of acoustic waveforms formed from a single transmit signal interfere to produce a single transmit beam. Using four-line multi-line transmit with 64 transducer elements as an example, each element converts four individual transmit signals into four acoustic waveforms; the 64 waveforms associated with an individual transmit signal form an individual transmit beam sharing the waveform characteristics of the transmit signal. The individual transmit beams may form a combined beam with a reduced peak negative pressure, reduced spatial-peak time-average intensity, reduced total acoustic output power, reduced mechanical index, or the like throughout the tissue due to the time delay adjustments determined at 710 and applied at 715. The transmit beams reflect off structures in the body and return to the transducer elements 104, which convert the acoustic echoes into electrical signals. The electrical signals may be time delayed by the receiver 108 to temporally align the echo signals according to the time delays determined at 710 and applied at 715. Receive beamformer 110 may sum the echo signals to produce a receive signal. There may be one or more receive signals corresponding to each transmit signal. Processor 116 may process the receive signals in order to account for the different waveform shapes of the transmit beams, if any, when generating the resulting ultrasound image. Processing the receive signals may include converting the ultrasound data into at least one image for display using signal processing techniques such as time-gain compensation, compression, gray-scale mapping, and spatial compounding. The image or images may then be displayed on a display device 118. Method 700 may then end.

In one embodiment, more than one pulse parameter may be adjusted for one or more transmit beams relative to the pulse parameters of the other transmit beams in the same multi-line transmit event. For example, both the frequency and the phase of one or more transmit beams may be shifted with respect to the other transmit beams, both the phase and the delay lines of one or more transmit beams may be adjusted with respect to the other transmit beams, or both the frequency and the delay lines of one or more transmit beams may be adjusted with respect to the other transmit beams. As discussed above with regard to FIG. 6, adjusting the delay lines of one or more transmit beams may include changing the configuration of delay lines, shifting the focal depth of one or more transmit beams, and combinations thereof. For example, the phase shifts of one or more transmit beams may be adjusted to reduce the mechanical index, and the delay line configuration may be adjusted to account for the phase shifted transmit beams so that the mechanical index can be further reduced.

In this way, by adjusting a waveform shape and/or delay line configuration of one or more transmit beams in a same multi-line transmit event a technical effect of reducing an acoustic output power, and/or an averaged intensity, and/or a thermal index, and the like of a combined beam formed from all the transmit beams in the same multi-line transmit event is achieved. By reducing the acoustic intensity of the resulting combined beam, tissue degradation or other detrimental health effects may be reduced compared to multi-line transmits where all the transmit beams have the same waveform shape with one element simultaneously transmitting all pulses in the multi-line transmit event or the peak pressure and/or intensity occurs in the normal to the transducer surface and close to it.

Furthermore, adjusting a delay line configuration of one or more transmit beams in a same multi-line transmit event may offer hardware advantages. In conventional multi-line transmit, transmit beamformer 101 is limited in its output voltage. If the center element needs, for example, four times the amplitude of its neighboring elements, the neighboring elements can only transmit at 25% capacity, thereby decreasing overall acoustic energy and image quality. However, when adjusting a delay line configuration of one or more transmit beams in a same multi-line transmit event in accordance with the current disclosure, the neighboring elements can be driven at 50% capacity, thereby increasing the signal-to-noise ratio.

As one embodiment, a method for ultrasound imaging comprises reducing an intensity at a position away from an array transducer of a combined beam formed from a plurality of transmit beams emitted by an array transducer in a multi-line transmit event by selectively adjusting one or more pulse parameters of one or more individual transmit beams of the combined beam for a given energy level of the one or more individual transmit beams. In one example, the one or more pulse parameters includes a phase shift and selectively adjusting the one or more pulse parameters of the one or more individual transmit beams of the combined beam includes changing a shape of the one or more individual transmit beams. For example, the shape of the one or more individual transmit beams may have a maximal amplitude offset from a maximal amplitude of an unadjusted individual transmit beam. In another example, the shape of the one or more individual transmit beams may have a maximal amplitude offset from a maximal amplitude of a differently adjusted individual transmit beam.

The method further comprises transmitting the plurality of transmit beams in the multi-line transmit event with the array transducer, the array transducer including a plurality of elements. In another example, the one or more pulse parameters includes a delay line, the delay line determining an excitation sequence of the plurality of elements to form a directed transmit beam. Selectively adjusting the one or more pulse parameters of the one or more individual transmit beams of the combined beam comprises adjusting the delay line of each of the one or more individual transmit beams so that each delay line intersects pairwise while maintaining a same focal depth and a same duration of the multi-line transmit event.

In one example, the array transducer includes a plurality of elements adjacently arranged in a one-dimensional array. In another example, the array transducer includes a plurality of elements adjacently arranged in a two-dimensional array.

In yet another example, selectively adjusting the one or more pulse parameters of one or more individual transmit beams of the combined beam includes adjusting a frequency of the one or more individual transmit beams relative to other beams of the plurality of transmit beams, wherein an attenuation coefficient of each individual transmit beam of the combined beam is within a threshold range. Additionally or alternatively, adjustment for different attenuation coefficients may be implemented on the transmission and or on receive.

In another example, selectively adjusting the one or more pulse parameters of the one or more individual transmit beams of the combined beam includes adjusting a focal depth of the one or more individual transmit beams relative to other beams of the plurality of transmit beams. Adjusting the focal depth of the one or more individual transmit beams includes changing a curvature of a delay line associated with the one or more individual transmit beams.

Further, selectively adjusting the one or more pulse parameters of the one or more individual transmit beams of the combined beam includes selecting different pulse parameters for the one or more individual transmit beams to reduce one or more acoustic parameters of interference, such as mechanical index, between the plurality of transmit beams.

As another embodiment, a method for ultrasound imaging comprises selectively adjusting a waveform shape of one or more transmit beams of a plurality of transmit beams relative to the waveform shape of other transmit beams of the plurality of transmit beams, and transmitting the plurality of transmit beams with an array transducer during a same multi-line event.

The method further comprises generating the one or more transmit beams by applying a pulse profile to the array transducer. In one example, selectively adjusting the waveform shape of one or more transmit beams of the plurality of transmit beams includes selectively adjusting a phase shift of a sinusoidal term of the pulse profile.

In another example, selectively adjusting the waveform shape of one or more transmit beams of the plurality of transmit beams includes adjusting a phase shift of each individual transmit beam of the plurality of transmit beams relative to the phase shift of the other transmit beams of the plurality of transmit beams.

Further, selectively adjusting the waveform shape of one or more transmit beams of the plurality of transmit beams includes selecting a different phase shift for the one or more transmit beams to reduce a mechanical index of interference between the plurality of transmit beams.

In another example, selectively adjusting the waveform shape of one or more transmit beams of the plurality of transmit beams includes offsetting a maximal amplitude of the waveform shape of the one or more transmit beams from a maximal amplitude of the waveform shape of an unadjusted transmit beam of the plurality of transmit beams.

As yet another embodiment, a system for ultrasound imaging comprises an array transducer including a plurality of array elements, the array transducer adapted to transmit a plurality of transmit beams in a multi-line transmit event; a transmitter coupled to the array transducer and adapted to apply a separate signal pulse to each array element of the plurality of array elements; a receiver coupled to the array transducer and adapted to receive an echo signal produced by each array element and to form a receive signal by summing separate echo signals produced by each array element; a processor coupled to the receiver and adapted to process the set of signals to account for differences in the separate signal pulse and to produce an output signal comprising a sum of the processed set of signals, the processor further configured with computer readable instructions for selectively adjusting a time delay applied to each of the separate signal pulses so that no single transducer element simultaneously transmits each of the plurality of transmit beams.

In one example, the controller further includes computer readable instructions for selectively adjusting the time delay applied to each of the separate signal pulses so that each transmit beam of the plurality of transmit beams has a same focal depth.

In another example, the controller further includes computer readable instructions for adjusting the time delay applied to each of the separate signal pulses so that a single transducer element simultaneously transmits at most a number of individual transmit beams of the plurality of transmit beams, wherein the number of individual transmit beams is less than a total number of individual transmit beams of the plurality of transmit beams. For example, if the total number of individual transmit beams of the plurality of transmit beams is four, a single transducer element may simultaneously transmit at most three individual transmit beams. In another example, if the total number of individual transmit beams of the plurality of transmit beams is eight, a single transducer element may simultaneously transmit at most seven individual transmit beams.

In yet another example, the controller further includes computer readable instructions for adjusting the time delay applied to each of the separate signal pulses to reduce one or more acoustic parameters of interference between the plurality of transmit beams, such as mechanical index, below a threshold level.

In one example, the plurality of array elements are adjacently arranged in a one-dimensional array. In another example, the plurality of array elements are adjacently arranged in a two-dimensional array and the processor further includes computer readable instructions for increasing a total transmit time of the multi-line transmit event.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for ultrasound imaging, comprising:
reducing an intensity at a position away from an array transducer of a combined beam formed from a plurality of transmit beams emitted by the array transducer in a multi-line transmit event by selectively adjusting one or more pulse parameters of one or more individual transmit beams of the combined beam for a given energy level of the one or more individual transmit beams, each of the plurality of transmit beams formed from a corresponding plurality of ultrasonic pulses generated by the array transducer during the multi-line transmit event, the array transducer including a plurality of elements, wherein a transducer element of the array transducer simultaneously transmits two or more ultrasonic pulses during the multi-line transmit event, each of the two or more ultrasonic pulses corresponding to different transmit beams of the plurality of transmit beams, wherein the one or more pulse parameters includes a delay line, the delay line determining an excitation sequence of the plurality of elements to form a directed transmit beam, wherein selectively adjusting the one or more pulse parameters of the one or more individual transmit beams of the combined beam comprises adjusting the delay line of each of the one or more individual transmit beams so that each delay line intersects pairwise while maintaining a same focal depth and a same duration of the multi-line transmit event.

2. The method of claim 1, wherein the one or more pulse parameters includes a phase shift and wherein selectively adjusting the one or more pulse parameters of the one or more individual transmit beams of the combined beam includes changing a shape of the one or more individual transmit beams, the shape of the one or more individual transmit beams having a maximal amplitude offset from a maximal amplitude of an unadjusted individual transmit beam.

3. The method of claim 1, wherein the array transducer includes the plurality of elements adjacently arranged in a two-dimensional array.

4. The method of claim 1, wherein selectively adjusting the one or more pulse parameters of the one or more individual transmit beams of the combined beam includes adjusting a frequency of the one or more individual transmit beams relative to other beams of the plurality of transmit beams.

5. The method of claim 1, wherein selectively adjusting the one or more pulse parameters of the one or more individual transmit beams of the combined beam includes adjusting a focal depth of the one or more individual transmit beams relative to other beams of the plurality of transmit beams, wherein adjusting the focal depth of the one or more individual transmit beams includes changing a curvature of a delay line associated with the one or more individual transmit beams.

6. The method of claim 1, wherein selectively adjusting the one or more pulse parameters of the one or more individual transmit beams of the combined beam includes selecting different pulse parameters for the one or more individual transmit beams to reduce constructive interference between the plurality of transmit beams.

7. A method for ultrasound imaging, comprising:
reducing an intensity at a position away from an array transducer of a combined beam formed from a plurality of transmit beams emitted by the array transducer in a multi-line transmit event by selectively adjusting one or more pulse parameters of one or more individual transmit beams of the combined beam for a given energy level of the one or more individual transmit beams, each of the plurality of transmit beams formed from a corresponding plurality of ultrasonic pulses generated by the array transducer during the multi-line transmit event, further comprising transmitting the plurality of transmit beams in the multi-line transmit event with the array transducer, the array transducer including a plurality of elements, and wherein the one or more pulse parameters includes a delay line, the delay line determining an excitation sequence of the plurality of elements to form a directed transmit beam, wherein selectively adjusting the one or more pulse parameters of the one or more individual transmit beams of the combined beam comprises adjusting the delay line of each of the one or more individual transmit beams so that each delay line intersects pairwise while maintaining a same focal depth and a same duration of the multi-line transmit event.

8. A method for ultrasound imaging, comprising:
reducing an intensity at a position away from an array transducer of a combined beam formed from a plurality of transmit beams emitted by the array transducer in a multi-line transmit event by selectively adjusting one or more pulse parameters of one or more individual transmit beams of the combined beam for a given energy level of the one or more individual transmit beams, each of the plurality of transmit beams formed from a corresponding plurality of ultrasonic pulses generated by the array transducer during the multi-line transmit event, further comprising transmitting the plurality of transmit beams in the multi-line transmit event with the array transducer, the array transducer including a plurality of elements, and wherein the one or more pulse parameters includes a delay line, the delay line determining an excitation sequence of the plurality of elements to form a directed transmit beam, wherein the array transducer includes the plurality of elements adjacently arranged in a one-dimensional array, and wherein a duration of the multi-line transmit event equals a longest time delay applied to one of the plurality of ultrasonic pulses, the duration on the order of microseconds.

9. A method for ultrasound imaging, comprising:
selectively adjusting each of a delay line and a waveform shape of one or more transmit beams of a plurality of transmit beams relative to a delay line and waveform shape of other transmit beams of the plurality of transmit beams; and
transmitting a combined beam comprising the plurality of transmit beams with an array transducer during a same multi-line event, each of the plurality of transmit beams formed from a corresponding plurality of ultrasonic pulses generated by the array transducer, wherein a transducer element of the array transducer simultaneously transmits two or more ultrasonic pulses during the multi-line event, each of the two or more ultrasonic pulses corresponding to different transmit beams of the plurality of transmit beams.

10. The method of claim 9, further comprising generating the one or more transmit beams by applying a pulse profile to the array transducer and wherein selectively adjusting the waveform shape of one or more transmit beams of the plurality of transmit beams includes selectively adjusting a phase shift of a sinusoidal term of the pulse profile.

11. The method of claim 9, wherein selectively adjusting the waveform shape of one or more transmit beams of the plurality of transmit beams includes adjusting a phase shift of each individual transmit beam of the plurality of transmit beams relative to a phase shift of the other transmit beams of the plurality of transmit beams.

12. The method of claim 9, wherein selectively adjusting each of the delay line and the waveform shape of one or more transmit beams of the plurality of transmit beams includes selecting a different delay line of the array transducer and a different phase shift for the one or more transmit beams based on a selected acoustic pressure threshold, wherein the combined beam formed from the plurality of transmit beams in the same multi-line event has an acoustic pressure below the selected acoustic pressure threshold.

13. The method of claim 9, wherein selectively adjusting the waveform shape of one or more transmit beams of the plurality of transmit beams includes offsetting a maximal amplitude of the waveform shape of the one or more transmit beams from a maximal amplitude of a waveform shape of an unadjusted transmit beam of the plurality of transmit beams.

14. A system for ultrasound imaging, comprising:
an array transducer including a plurality of array elements, the array transducer adapted to transmit a combined beam comprising a plurality of transmit beams in a multi-line transmit event, each of the plurality of transmit beams in the multi-line transmit event comprising a corresponding plurality of ultrasonic pulses generated by the plurality of array elements, wherein an array element of the plurality of array elements simultaneously transmits two or more ultrasonic pulses during the multi-line transmit event, each of the two or more ultrasonic pulses corresponding to different transmit beams of the plurality of transmit beams;
a transmitter coupled to the array transducer and adapted to apply a separate signal pulse to each array element of the plurality of array elements;
a receiver coupled to the array transducer and adapted to receive an echo signal produced by each array element and to form a receive signal by summing separate echo signals produced by each array element; and
a processor coupled to the receiver and adapted to process a set of receive signals received from the receiver to account for differences in the separate signal pulses and to produce an output signal comprising a sum of the processed set of receive signals, the processor further configured with computer readable instructions for selectively adjusting a time delay applied to each of the separate signal pulses so that no single transducer element simultaneously transmits each of the plurality of transmit beams of the combined beam, wherein the processor further includes computer readable instructions for adjusting the time delay applied to each of the separate signal pulses so that a single transducer element simultaneously transmits at most a number of individual transmit beams of the plurality of transmit beams, wherein the number of individual transmit beams is less than a total number of individual transmit beams of the plurality of transmit beams.

15. The system of claim 14, wherein the processor further includes computer readable instructions for selectively adjusting the time delay applied to each of the separate signal pulses so that each transmit beam of the plurality of transmit beams has a same focal depth.

16. The system of claim 14, wherein the processor further includes computer readable instructions for adjusting the time delay applied to each of the separate signal pulses to reduce a mechanical index of interference between the plurality of transmit beams below a threshold level.

17. The system of claim 14, wherein the plurality of array elements is adjacently arranged in a one-dimensional array, and wherein the processor further includes computer readable instructions for adjusting waveform shapes of the plurality of transmit beams to reduce an amplitude of the combined beam in a region adjacent to the plurality of array elements.

18. The system of claim 14, wherein the plurality of array elements is adjacently arranged in a two-dimensional array and wherein the processor further includes computer readable instructions for increasing a total transmit time of the multi-line transmit event.

* * * * *